(12) United States Patent
McCarthy

(10) Patent No.: US 6,360,929 B1
(45) Date of Patent: Mar. 26, 2002

(54) MEDICINAL ATOMIZING INHALER POUCH/RETAINER

(76) Inventor: Madeleine McCarthy, 671 High St., Hanson, MA (US) 02341

( * ) Notice: Subject to any disclaimer, the term of this patent is extended or adjusted under 35 U.S.C. 154(b) by 9 days.

(21) Appl. No.: 09/617,830

(22) Filed: Jul. 17, 2000

(51) Int. Cl.⁷ .................................................. A45F 5/00
(52) U.S. Cl. ...................... 224/251; 224/194; 224/254; 224/269; 224/677
(58) Field of Search ................................ 224/251, 194, 224/195, 240, 250, 677, 254, 269, 271

(56) References Cited

U.S. PATENT DOCUMENTS

| | | | | |
|---|---|---|---|---|
| 3,908,875 A | * | 9/1975 | Wilson et al. .......... 224/254 X |
| 5,392,975 A | * | 2/1995 | Blankenship, Jr. .......... 224/253 |
| 5,429,075 A | * | 7/1995 | Passarella et al. .......... 119/795 |
| 5,477,999 A | * | 12/1995 | Blankenship, Jr. .......... 224/253 |
| D375,624 S | * | 11/1996 | Jensen .......................... D3/229 |
| 5,833,093 A | * | 11/1998 | Honaker et al. ............. 224/175 |
| 5,855,307 A | * | 1/1999 | Biddick et al. .............. 224/267 |
| 6,196,431 B1 | * | 3/2001 | Underhill ..................... 224/237 |

* cited by examiner

*Primary Examiner*—Stephen K. Cronin
(74) *Attorney, Agent, or Firm*—Charles I. Brodsky

(57) ABSTRACT

A decorative medicinal atomizing inhaler pouch providing a manner for securement to a user's apparel or person, for fast and easy access, and to alow physical exercise and sports without the need to wear a purse/pack to store it in. In a preferred embodiment, a flexible water resistant fabric is used to encase the inhaler, snugly forming to its contours, having an opening at one end to permit the mouthpiece of the inhaler to extend therethrough, and a second opening at its opposite end to permit the top of the inhaler and its inserted medicine canister to protrude unimpeded to permit its intended operation. Along the lateral section of one embodiment of the pouch is a retention clip designed to attach to a belt, waistband, pocket or a variety of other points; in a second embodiment, an elastic strap is integrated into the pouch.

12 Claims, 1 Drawing Sheet

MEDICINAL ATOMIZING INHALER POUCH/RETAINER

BACKGROUND OF THE INVENTION

1. Field of the Invention

This invention relates to medicinal atomizing inhalers of the kind typically used by asthmatics to inhale pre-measured doses of medications. More particularly, it relates to a decorative pouch/retainer for keeping an inhaler readily accessible during physical exercise and participation in sports. Experience has shown that wearing a fanny-type pack is both cumbersome and generally difficult to access during a severe asthma attack.

2. Description of the Related Art

As is well known in the medicinal atomizer industry, it is imperative that an asthmatic have immediate access to his inhaler at all times of the day, as during an attack, the inability to breath quickly disables the person. Although going out in the cold, physical exertion and outdoor recreation can bring about an attack, a majority of asthmatics refuse to let their condition prevent them from enjoying those aspects of their lives. Thus, joggers typically store their inhalers in a fanny-type pack, or some other creative location, while swimmers have even fewer places to put their inhalers—and usually end up leaving them on leaving them on the towels at poolside or on the beach. Children, however, are not as careful, or fast acting in locating their inhalers, often forgetting where they were left. As is also known, carrying the inhaler can be so intrusive during physical activities that it is either left behind or kept in a place difficult to access, resulting in unnecessarily severe attacks and emergencies.

As will be understood, these inhalers are typically designed for function and reliability, and not for aesthetics. Thus, several attempts have been made to improve the appearance of the inhaler—either by forming its case with curves and bulges, or by having a decorative mold—such as a Bart Simpson head—in which the inhaler fits for storage when not being used. These latter approaches, though, result in a larger item to carry about, and typically require the user to first remove the inhaler from the mold before use during an attack.

OBJECTS OF THE INVENTION

It is an object of the invention, therefore, to provide a new and improved medicinal atomizing inhaler pouch that is aesthetically appealing.

It is an object of the invention, also, to provide such a pouch which is not harmed if submerged in water.

It is also an object of the invention, to prevent the misplacement and loss of a medicinal atomizing inhaler.

It is another object of the invention to provide a pouch of this type which secures to a user's apparel or person in an unobtrusive manner, and which permits fast retrieval.

It is a further object of the invention to provide such a pouch inexpensively enough for people to purchase several to coordinate with the apparel which they may be wearing.

SUMMARY OF THE INVENTION

As will become clear from the following description, the new and improved medicinal atomizing inhaler pouch embodying the invention easily secures to a user's apparel or person in an unobtrusive manner enabling its constant presence throughout the day, more specifically, during physical activities, either on land, or in the water. As will also be seen, the medicinal atomizing inhaler pouch of the invention accomplishes this in a manner which is aesthetically pleasing, and which removes an additional deterrent to having the inhaler in a visible place, an important consideration for children embarrassed by the need to use one.

Thus, and in accordance with the invention, the inhaler pouch is constructed of an elastic water proof fabric—such as nylon or neopren—having a decorative print on its exterior surface. The pouch is designed to be of similar shape to the inhaler, and constructed with an interior dimension slightly smaller than the inhaler to create a snug fit once it is stretched to permit insertion. As will be seen, the pouch is open at either end to permit the inhaler to operate without removal therefrom. In a preferred embodiment, the pouch is secured to the user's apparel or person by an appropriate fastener—for example, a compression clip located on its lateral edge, or via an integrated elastic strap.

BRIEF DESCRIPTION OF THE DRAWINGS

These and other features of the invention will be more clearly understood from a consideration of the following description, taken in connection with the accompanying drawings in which.

DETAILED DESCRIPTION OF THE INVENTION

Figure 1:
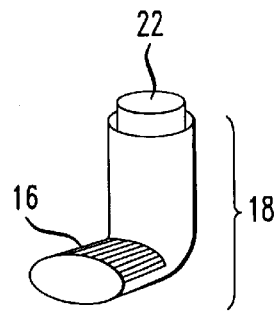
FIG. 1 is a front perspective view showing a medicinal atomizing inhaler with a medicinal canister installed in place.
Figure 2:
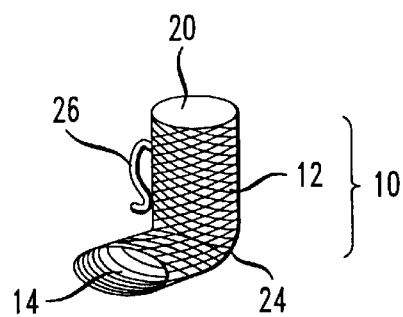
FIG. 2 is a side perspective view of the inhaler pouch showing a decorative exterior pattern, with dimensions slightly smaller than that of the medicinal atomizing inhaler.
Figure 3:
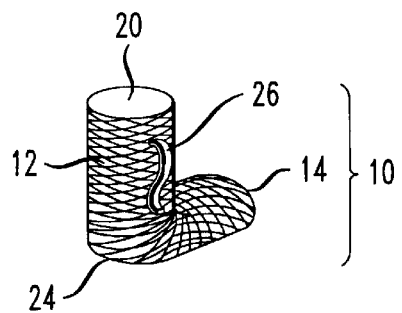
FIG. 3 is a rear perspective view of the inhaler pouch of FIG. 2, showing a compression clip used to attach the pouch to a user's apparel—such a to his belt, wasteband, or pocket.
Figure 4:
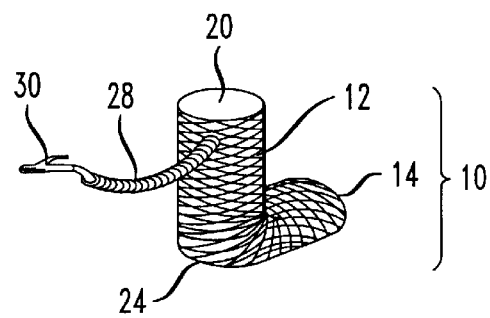
FIG. 4 is a rear perspective view of the inhaler pouch of FIG. 2, showing an integrated elastic strap for attaching the pouch to a users apparel or person—such as to a zipper tab, or around the user's wrist.
Figure 5:
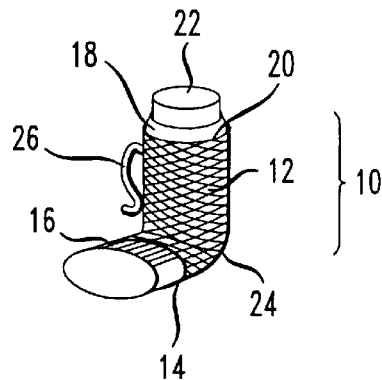
FIG. 5 is a front perspective view of the inhaler pouch of FIG. 2, showing the medicinal atomizing inhaler properly installed within the pouch.

As will be seen from the drawings, the medicinal atomizing inhaler pouch 10 according to the invention includes a water-proof elastic fabric tube 12 having a lower aperture 14 to permit the mouthpiece 16 of the inhaler 18 to protrude outwardly to permit insertion in the mouth of the user with his lips tightly sealed around the mouthpiece 16 directly. Located at the opposite end of the fabric tube 12 is an upper aperture 20 to permit the top lip of the inhaler 18 (and the installed medicinal canister 22) to protrude upwardly from the pouch 10 for actuation by the user, and to permit the mixture of the medicine with air. The tube 12 is constructed with an elbow bend 24 towards the lower aperture 14, coinciding with the bend in a typical inhaler 18. In a preferred embodiment the tube 12 is elastic in all directions. The elastic fabric tube 12 is to be assembled using a fabric which can survive hours of submersion in salt water and/or chlorinated water without discoloration or wear—such as synthetics and neoprene. In accordance with the invention, the tube 12 is manufactured to have a smaller internal diameter than the exterior dimension of the inhaler 18. As the fabric tube 12 is elastic, the pouch 10 then will stretch to snugly fit any number of inhaler designs which utilize a standard medicinal canister. Additionally, the fabric tube 12 is of a short enough length so that the upper aperture 20 does not extend beyond the top of the inhaler 18, so as to permit air to be drawn into the inhaler and mixed with the contents of the medicinal canister 22. Due to the insignificant increase to the size of the inhaler 18 when installed in the pouch 10, the user has no need to remove the pouch to put it in a traditional storage place such as a purse. If the user intends to remove the pouch 10, to exchange it with another having a different decorative design, on its outer surface, for example, he or she merely pulls at the top of the fabric tube 12, sliding it off the inhaler 18.

Integrated into the lateral aspect of the fabric tube 12 is a spring type compression clip 26 according to a preferred embodiment, having a natural quiescent closed state. When the compression clip 26 is slid over a piece of apparel—such as the waistband of swim trunks—the pressure of the spring action holds the pouch 10 in place. The user need only pull upwardly on the pouch 10, to remove it from the piece of apparel, immediately placing it into the mouth for use. In a second embodiment, a coiled strap 28 serves as the fastener integrated into the pouch 10, having a clasp 30 at its end to permit securement to alternative items such as a zipper tab, the user's wrists, etc. Such clasp may also be constructed of a non-corrosive material.

In the use of the invention, the user merely pulls the fabric tube 12 of the pouch 10 over the inhaler 18 until the top of the inhaler 18 extends through the upper aperture 20. The user need only clip the pouch onto an item they are bringing with them, without the need for any bulky carrying cases. This is especially useful during physical activities, where carrying cases cannot be used. The coiled strap 28 is particularly useful in preventing children from misplacing the inhaler 18. This strap 28 is of a length and elasticity which permits the asthma sufferer to use the inhaler 18, without unfastening it from its attachment point. If a child were storing it in his jacket pocket, for example, then if it fell out of the pocket by accident, it would not be lost.

While there have been described what are considered to be preferred embodiments of the present invention, it will be readily appreciated by those skilled in the art that modifications can be made without departing from the scope of the teachings herein. For example, while a clasp is described to secure to zipper tabs or wrists, an alternative securing arrangement, (such as Velcro) could be employed for even a greater variety of placements. For at least such reason, therefore, resort should be had to the claims annexed hereto for a true understanding of the scope of the invention.

I claim:

1. A medicinal atomizing inhaler pouch/retainer comprising a flexible tube having an upper aperture for the insertion of a medicinal inhaler while protruding therefrom; a lower aperture on said flexible tube for permitting a mouthpiece of said inhaler to extend therethrough; and fastening means integrated into staid flexible tube for securement to a users apparel or person;s wherein said flexible tube is elastic in all directions; and wherein said flexible tube includes an elbow bend towards a lower end thereof.

2. The medicinal atomizing inhaler pouch/retainer of claim 1 wherein said flexible tube is of a quiescent interior dimension smaller than that of the medicinal inhaler to be inserted therein.

3. The medicinal atomizing inhaler pouch/retainer of claim 1 wherein said flexible tube is of a length shorter than the length of said inhaler to permit both a top of said inhaler, and the mouthpiece located at its lower end to extend therefrom.

4. The medicinal atomizing inhaler pouch/retainer of claim 1 wherein said flexible tube is constructed of a water-proof elastic material unaffected by exposure to salt or chlorine.

5. The medicinal atomizing inhaler pouch/retainer of claim 4 wherein said elastic material includes a decorative color/design scheme on an outer surface thereof.

6. The medicinal atomizing inhaler pouch/retainer of claim 1 wherein said fastening means comprises a compression clip.

7. The medicinal atomizing inhaler pouch/retainer of claim 6 wherein said compression clip is constructed of a non-corrosive material having a natural quiescent closed state.

8. The medicinal atomizing inhaler pouch/retainer of claim 6 wherein said compression clip is of a dimension large enough to secure said flexible tube to a piece of apparel while the user engages in physical activities, or other ordinary daily usages.

9. The medicinal atomizing inhaler pouch/retainer of claim 1 wherein said fastening means comprises a coiled strap.

10. The medicinal atomizing inhaler pouch/retainer of claim 9 wherein said coiled strap is constructed of a water-proof elastic material unaffected by exposure to salt or chlorine.

11. The medicinal atomizing inhaler pouch/retainer of claim 9 wherein said coiled strap includes a clasp at one end for securing to a user's apparel or person.

12. The medicinal atomizing inhaler pouch/retainer of claim 11 wherein said coiled strap is of a length and elasticity to permit a user to utilize said inhaler without first having to detach said clasp from its secured placement.

* * * * *